United States Patent [19]

Jernberg

[11] Patent Number: 5,059,123

[45] Date of Patent: Oct. 22, 1991

[54] PERIODONTAL BARRIER AND METHOD FOR AIDING PERIODONTAL TISSUE REGENERATION

[76] Inventor: Gary R. Jernberg, Mankato, Minn.

[21] Appl. No.: 600,191

[22] Filed: Oct. 18, 1990

Related U.S. Application Data

[63] Continuation-in-part of Ser. No. 522,999, May 14, 1990.

[51] Int. Cl.$^5$ .............................................. A61C 5/00
[52] U.S. Cl. ................................... 433/215; 433/229; 424/426; 424/435
[58] Field of Search .................... 433/215, 217.1, 136, 433/80, 229; 604/285, 286, 288, 890.1, 891.1, 892.1, 54, 49, 77; 128/DIG. 8; 606/151, 154; 424/426, 435, 444

[56] References Cited

U.S. PATENT DOCUMENTS

| | | | |
|---|---|---|---|
| 4,226,848 | 10/1980 | Nagai et al. | 424/19 |
| 4,249,531 | 2/1981 | Heller et al. | 424/33 |
| 4,292,299 | 9/1981 | Suzuki et al. | 424/16 |
| 4,321,711 | 3/1982 | Mano | 3/1.4 |
| 4,524,065 | 6/1985 | Pinnell | 424/94 |
| 4,536,387 | 8/1985 | Sakamoto et al. | 424/14 |
| 4,568,536 | 2/1986 | Kronenthal et al. | 424/22 |
| 4,645,668 | 2/1987 | Pinnell | 424/95 |
| 4,650,665 | 3/1987 | Kronenthal et al. | 424/435 |
| 4,657,548 | 4/1987 | Nichols | 623/10 |
| 4,685,883 | 8/1987 | Jernberg | 433/215 |
| 4,703,108 | 10/1989 | Silver et al. | 530/356 |
| 4,713,243 | 12/1987 | Schiraldi et al. | 424/151 |
| 4,745,161 | 5/1988 | Saudek et al. | 525/420 |
| 4,764,377 | 8/1988 | Goodson | 424/435 |
| 4,776,890 | 10/1988 | Chu | 106/161 |
| 4,780,320 | 10/1988 | Baker | 424/493 |
| 4,789,662 | 12/1988 | Thomas-Leurquin et al. | 514/21 |
| 4,789,663 | 12/1988 | Wallace et al. | 514/21 |
| 4,795,467 | 1/1989 | Piez et al. | 623/16 |
| 4,816,339 | 3/1989 | Tu et al. | 428/421 |
| 4,828,563 | 5/1989 | Muller-Lierheim | 623/16 |
| 4,837,285 | 6/1989 | Berg et al. | 530/356 |
| 4,839,175 | 6/1989 | Guo et al. | 424/450 |
| 4,841,962 | 6/1989 | Berg et al. | 128/156 |
| 4,851,521 | 7/1989 | della Valle et al. | 536/55.1 |
| 4,886,787 | 12/1989 | de Belder et al. | 514/57 |
| 4,892,516 | 1/1990 | Harle | 604/288 |

FOREIGN PATENT DOCUMENTS

| | | |
|---|---|---|
| 3060463 | 10/1987 | European Pat. Off. . |
| 87/00272 | 12/1987 | PCT Int'l Appl. . |
| 146525A | 4/1985 | United Kingdom . |

OTHER PUBLICATIONS

M. Minabe et al., 60, *J. Periodontal,* 113–117 (Feb. 1989).

I. Aukhil et al., 18, *Journal of Periodontal Research,* 643–654 (1983).

S. Nyman et al., 9, *Journal of Clinical Periodontology,* 290–296 (1982).

I. Magnusson et al., 20, *Journal of Periodontal Research,* 201–208 (1985).

F. Isidor et al., 12, *Journal of Clinical Periodontology,* 728–735 (1985).

J. Gottlow et al., 11, *Journal of Clinical Periodontology,* 494–503 (1984).

S. Nyman et al., 9, *Journal of Clinical Periodontology,* 257–265 (1982).

S. Nyman et al., 7, *Journal of Clinical Periodontology,* 394–401 (1980).

T. Karring et al., 7, *Journal of Clinical Periodontology,* 96–105 (1980).

J. Caton et al., 7, *Journal of Clinical Periodontology,* 224, 231 (1980).

S. Nyman et al., 22, *Journal of Periodontal Research,* 252–254 (1987).

R. Caffesse et al., 59, *J. Periodontal.,* 589–594 (Sep. 1988).

R. Pontoriero et al., 15, *J. Clin. Periodontol,* 247–254 (1988).

W. Becker et al., 58, *J. Periodontol.,* 819–826 (Dec. 1987).

R. Pontoriero et al., 14, *J. Clin. Periodontol,* 618–620 (1987).

J. Gottlow et al., 13, *J. Clin Periodontol,* 604–616 (1986).

A. Melcher, 47, *Journal of Periodontology,* 256–260 (1976).

F. Isidor et al., 13, *J. Clin Periodontol,* 145–150 (1986).

R. Niederman et al., Abstract 1392 of Study Supported by NIDR Grant DE–07675 and W. L. Gore & Associates.

R. Niederman et al., Abstract 1278 of Study Supported by W. L. Gore & Associates.

R. Caffesse et al., Abstract 1391 of The Univ. of Mich. Sch. of Dent., Med. Sch. and V.A.M.C.

J. Gottlow et al., Abstract 1394 of University of Gothenburg, Sweden, and Royal Dental College, Aarhus, Denmark.

Exhibit A is a copy of an efficacy study reference for Vicryl periodontal barrier, copyright 1990.

Exhibit B is a copy of a use manual for Vicryl periodontal barrier, copyright 1990.

Exhibit C is a copy of a brochure entitled "Gore-Tex ® Periodontal Material in Extra-Large Configurations," copyright 1988.

Exhibit D is a copy of a brochure entitled "Gore-Rex ® Periodontal Material Performance Review," copyright 1988.

Exhibit E is a copy of a brochure entitled "Gore-Tex ® Periodontal Material," copyright 1987.

Exhibit F is a copy of a brochure entitled "Your Choice, Gore-Tex ® Periodontal Material for Guided Tissue Regeneration," copyright 1987.

*Primary Examiner*—Cary E. O'Connor
*Attorney, Agent, or Firm*—Merchant, Gould, Smith, Edell, Welter, et al.

[57] ABSTRACT

A periodontal barrier and method incorporating chemotherapeutic agents is disclosed for aiding and guiding periodontal tissue regeneration.

39 Claims, 3 Drawing Sheets

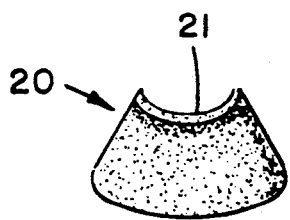 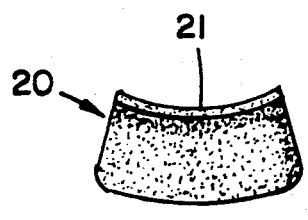 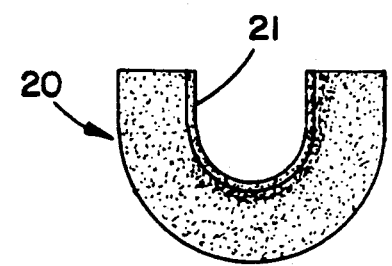
FIG. 2A  FIG. 2B  FIG. 2C
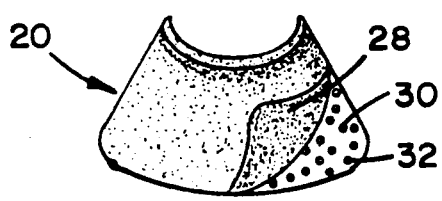
FIG. 3
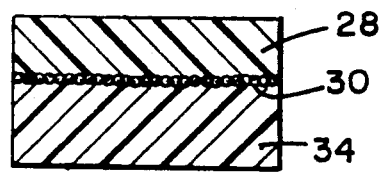
FIG. 4A
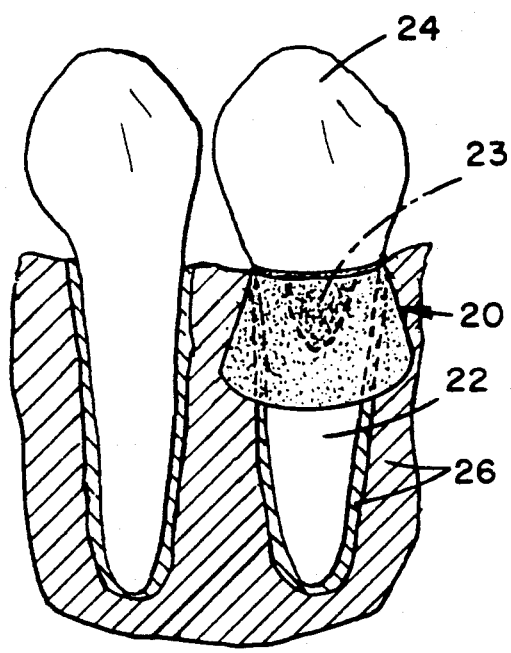
FIG. 1
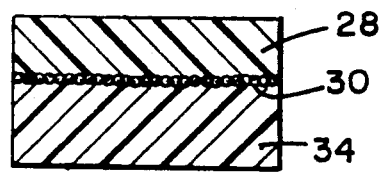
FIG. 4B
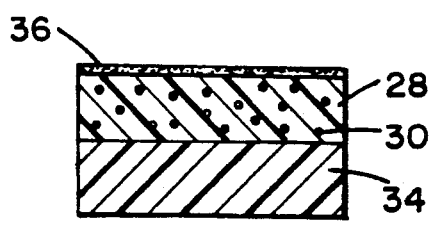
FIG. 4C
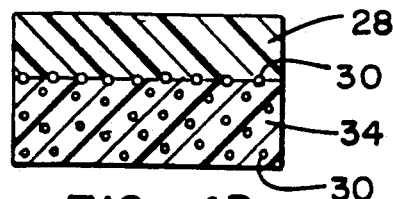
FIG. 4D

PERIODONTAL BARRIER AND METHOD FOR AIDING PERIODONTAL TISSUE REGENERATION

This Application is a Continuation-in-Part of U.S. Pat. Application Ser. No. 07/522,999, Filed May 14, 1990, pending.

TECHNICAL FIELD OF THE INVENTION

The present invention relates to a periodontal barrier and method, and in particular, a periodontal barrier and method for aiding periodontal tissue regeneration.

BACKGROUND OF THE INVENTION

Periodontal disease is a major concern in dentistry. Applicant's U.S. Pat. No. 4,685,883 deals with the treatment of periodontal and related diseases. Periodontal tissues are often lost with the progression of periodontal disease. Loss of periodontal tissue compromises the prognosis for retention of teeth in the dental arch, often creates an unhealthy environment in the mouth and may be unsightly.

Various methods have been used to facilitate regeneration of lost or diseased periodontal tissue. Periodontal barriers are sometimes surgically implanted adjacent the root of the tooth, or wherever tissue loss has occurred, by periodontal surgery to aid and guide tissue regeneration along the tooth surface where periodontal tissue regeneration is desired. Presently, these barriers are comprised of materials such as polytetrafluoroethylene (PTFE) which is biocompatible and non-resorbable. The barriers are typically removed after 4-6 weeks by a surgical re-entry procedure. Resorbable barriers are also being investigated for potential use in periodontal guided tissue regeneration. For example, cross-linked collagen is being studied in this regard.

It is often difficult to obtain the periodontal tissue growth desired since the regeneration of periodontal tissue is variable. Moreover, surgical implantation of barriers can be associated with infection and inflammation. Infection and excessive inflammation can adversely effect tissue regeneration with the use of periodontal barriers for guiding healing. Therefore it would be beneficial to be able to treat the tissue regeneration site with antibiotics, anti-inflammatories, or other appropriate chemotherapeutic agents as required to facilitate periodontal tissue regeneration. Also, the use of carrier agents in conjunction with appropriate chemotherapeutic agents to enhance cellular uptake of the chemotherapeutic agents would be helpful in the regeneration of periodontal tissue. Presently, applicant is not aware of chemotherapeutic agents being incorporated into these barriers to facilitate tissue regeneration.

A potential problem envisioned with the use of chemotherapeutic agents in conjunction with periodontal barriers is how to control and regulate the delivery and uptake of such agents to the tissue regeneration site over an extended predetermined period of time so as to obtain the desired periodontal tissue growth.

The apparatus and method of the present invention solves these and many other problems associated with the use of periodontal barriers for tissue regeneration. The present invention provides a barrier and method wherein microparticles are incorporated into the periodontal barrier, the microparticles microencapsulating the chemotherapeutic agents and optional carrier agents desired.

The use of microparticles containing chemotherapeutic agents is known. For example, in Applicant's U.S. Pat. No. 4,685,883, time-release, microencapsulated chemotherapeutic agents are utilized to provide localized treatment of periodontal disease. However, the microcapsules are deposited in the periodontal pocket or attached to a root surface of the tooth for treatment of the periodontal disease itself and are not incorporated into a barrier for aiding or guiding periodontal tissue regeneration.

SUMMARY OF THE INVENTION

The present invention relates to a periodontal barrier and method providing for sustained, controlled delivery and enhanced uptake of microencapsulated chemotherapeutic agents, incorporated into the barrier, to a periodontal tissue regeneration site so as to aid and guide periodontal tissue regeneration.

An advantage of the present invention is to provide a periodontal tissue regeneration barrier incorporating microparticles microencapsulating chemotherapeutic agents and optional carrier agents, which upon implantation provide for sustained, controlled delivery and improved cellular uptake of antibiotic, antiinflammatory and other appropriate agents to the regeneration site, such that the barrier can aid and guide the regeneration of diseased or lost periodontal tissue.

One embodiment of the present invention will provide a periodontal barrier including one or more kinds of microencapsulated chemotherapeutic agent.

Another embodiment of the present invention will provide for carrier agents in association with the microencapsulated chemotherapeutic agents to improve cellular uptake of the delivered chemotherapeutic agents.

Yet another embodiment of the present invention will provide for release of different kind of chemotherapeutic agents at different times.

Still another embodiment of the present invention will include a microencapsulated antibiotic and a microencapsulated anti-inflammatory agent.

These and various other advantages and features of novelty which characterize the invention are pointed out with particularity in the claims annexed hereto and forming a part hereof. However, for a better understanding of the invention, its advantages, and objects attained by its use, reference should be had to the drawings which form a further part hereof, and to the accompanying descriptive matter, in which there is illustrated and described a preferred embodiment of the invention.

BRIEF DESCRIPTION OF THE DRAWINGS

In the drawings, in which like reference numerals and letters indicate corresponding parts throughout the several views, FIG. 1 is a diagrammatic view of a periodontal barrier in accordance with the principles of the present invention positioned adjacent a tooth for aiding or guiding regeneration of periodontal tissue, the periodontal barrier incorporating time release microparticles encapsulating chemotherapeutic agents and optional carrier agents so as to provide controlled time release and enhanced cellular uptake thereof;

FIGS. 2A through 2C are diagrammatic illustrations illustrating varying configurations of periodontal barriers;

FIG. 3 is a diagrammatic illustration illustrating a layer of the periodontal barrier being pulled back so as to reveal the microparticles contained in the periodontal barrier;

FIGS. 4A through 4D are end sectional views of periodontal barriers illustrating alternate embodiments of periodontal barriers showing various methods of incorporation of the microparticles into the periodontal barriers;

DETAILED DESCRIPTION

Figures 5A, 5B, 5C, 5D:
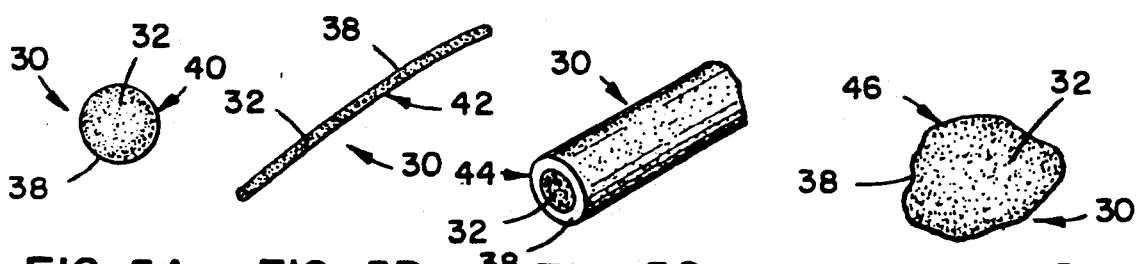
FIGS. 5A through 5D are diagrammatic perspective views of alternate configurations of the microparticles incorporated into the periodontal barrier and containing the chemotherapeutic and optional carrier agents.

Referring now to FIG. 1, there is diagrammatically illustrated an embodiment of a periodontal barrier 20 surgically positioned adjacent a root 22 of a tooth 24 to aid and guide periodontal tissue 26 regeneration, including bone and periodontal ligament, of a periodontal defect 23 adjacent the root 22 of the tooth 24. Periodontal barriers 20 of varying configurations are illustrated in FIGS. 2A through 2C. In FIG. 3, an outer layer 28 of the periodontal barrier 20 is shown pulled away to illustrate incorporation of time release microparticles 30 encapsulating chemotherapeutic and optional carrier agents 32 so as to provide controlled time release and enhanced cellular uptake thereof.

As noted, varying configurations of periodontal barriers, made of body compatible materials, including resorbable and noneresorbable materials are illustrated in FIGS. 2A through 2C. These general configurations are commonly used in existing periodontal barriers. The specific configuration of the periodontal barrier used will depend on the anatomy of the tooth root(s), the periodontal defect and the growth that is desired. FIG. 2A illustrates a barrier which might be used with a narrow tooth. FIG. 2B illustrates a barrier which might be used with a wide tooth. FIG. 2C illustrates a wraparound configuration. The sizes of the barriers might vary depending on the tooth size. Each illustrated barrier has a beaded rim 21, so as to provide a smoothed edge, which collars the crown-root junction of the tooth when surgically placed. The barriers are surgically implanted by conventional techniques and sutured in place by the use of body compatible sutures, such as GORE-TEX, a trademark of W. L. Gore & Associates, Inc.

The periodontal barrier of the present invention may incorporate microencapsulated chemotherapeutic agents and optional carrier agents into the body of the periodontal barrier in a variety of ways. In FIGS. 4A-4D there are illustrated cross-sectional views of alternate embodiments of barriers incorporating microencapsulated chemotherapeutic and optional carrier agents in accordance with the principles of the present invention. In particular, FIG. 4A depicts a cross-sectional view of a barrier according to the principles of the present invention, wherein one microencapsulated chemotherapeutic agent 30, such as an antibiotic, is incorporated into an inner layer 34 of the barrier. Conversely, another microencapsulated chemotherapeutic agent 30, such as an anti-inflammatory agent, is shown incorporated into an outer layer 28 of the barrier. In addition, it will also be appreciated that a carrier agent, in a microencapsulated, fluid or gel form, may be included with the microencapsulated chemotherapeutic agents to improve the cellular uptake of these chemotherapeutic agents at the periodontal treatment site.

In FIG. 4B, a single incorporation of microencapsulated chemotherapeutic agents 30 may be placed between the outer 28 and inner 34 layers of the barrier. In FIG. 4C, the microencapsulated chemotherapeutic agents are disposed throughout the top layer 28 of the barrier. In addition, a thin elastomer coating 36 is placed over this outer layer. In FIG. 4D, one type of microencapsulated chemotherapeutic agent 30 is disposed in the inner layer 34 while a second type of microencapsulated chemotherapeutic agent 30 is disposed between the inner 34 and outer 28 layers. It will be appreciated that there are other ways the microparticles and optional carrier agents might be incorporated into the barriers.

As diagrammatically illustrated in FIGS. 5A through 5D, the time-release microparticles 30 can have a variety of shapes and sizes so as to provide the desired rate and timed release of the chemotherapeutic and optional carrier agents 32 contained therein. The outer wall or matrix of the microparticles 38 is composed of a material allowing for the controlled, sustained release and enhanced cellular uptake of the chemotherapeutic and optional carrier agents over time upon diffusion through the material and/or degradation of the material.

The microparticles shown in FIGS. 5A through 5D are greatly enlarged, and in actual use, might typically be less than one millimeter in magnitude. As used herein, microparticles broadly include, without limitation, microspheres 40, microfibers or microfibrils 42, hollow microfibers 44, microsponges 46, as well as any other microshape which incorporate chemotherapeutic agents and optional carrier agents into their body or matrix.

In one embodiment, the microparticles are microspheres 40 having a spherical or near spherical shape as is generally illustrated in FIG. 5A, and are incorporated into the microstructure of the material comprising the periodontal barrier according to the present invention. For example, the microspheres can be contained within the mesh of fine fibrils connecting the matrix of nodes in expanded polytetrafluoroethylene (PTFE). In addition, somewhat larger microspheres can be meshed between layers of a multi-layered PTFE structure. The microspheres can be layered within the PTFE by adhesively positioning them onto the PTFE or by mixing them with a fluid and/or gel and flowing them into the netting or weave of the material. In such an embodiment, the fluid and gel can be carrier agents such as hyaluronic acid and a cross-linked gel of hyaluronic acid respectively. In yet another approach, microspheres can also be positioned between layers or coatings of the periodontal barrier 20 and between the barrier 20 and an elastomer coating 36 which might be covering the periodontal barrier.

In another embodiment, the microparticle may be in the form of microfibers or microfibrils 42 as is generally shown in FIG. 5B, which can be woven into the mesh of the periodontal barrier or, as described above, layered between successive layers of PTFE, or a similar material, comprising the periodontal barrier.

Alternatively, the microparticle may be in the form of a tubular member 44, or hollow microfiber, as is generally shown in FIG. 5C. As with microfibers or microfibrils, these hollow microfibers can be woven or layered into the body of the barrier.

In yet another embodiment, the microshapes may be in the form of microsponges, as is generally illustrated in FIG. 5D, which contain the desired chemotherapeutic agents within their own internal microchanneling.

Microspheres between 10 and 700 microns in diameter are preferred. Various chemical and physical methods for preparing microspheres have been developed over the past twenty-five years and are well known to those skilled in the art. In this regard, see for example Patrick B. Deasy, *Microencapsulation and Related Drug Processes*. Marcel Dekker Inc., N.Y., 1984. Coacervation, interfacial polymerization, solvent evaporation and spray drying are examples of methods used in the production of microspheres which incorporate chemotherapeutic and optional carrier agents. Similarly, microfibers or microfibrils can be obtained for layering or weaving into the barrier materials of the present invention. In this regard, hollow fibers ranging in size from 100 to 1,000 microns in diameter can be produced and drug loaded by extrusion.

A wide variety of chemotherapeutic agents can be incorporated into the microshapes employed according to the method of the present invention. For example, antibacterial agents such as the bisbiguanides, antibiotics such as vancomycin or tetracycline, anti-inflammatory agents such as indomethacin or hydrocortisone and tissue regenerative agents such as fibronectin may be employed, depending upon the particular treatment or regenerative goals sought.

Incorporation of the chemotherapeutic and optional carrier agents into the polymer comprising the microshape provides for a slow, sustained release of the chemotherapeutic agents and optional carrier agents. The polymer matrix or carrier material chosen is preferably biodegradable, pharmaceutically acceptable and available in various grades to allow for variable control of the release rate of different chemotherapeutic agents and optional carrier agents. In this regard, it will be appreciated that the biodegradable materials utilized in time release capsules taken orally or other suitable biodegradable materials safe for use in the body or commonly known may be employed. For example, various biocompatible polymers can be employed, including but not limited to, collagen, cellulosic polymers, ethylene vinyl acetate, methacrylate polymers, lactic-glycolic acid copolymers, polycaprolactone, etc. In addition, polymers such as polystyrene, polycarbonate, polysulfone, polylactides and polyurethane can be employed. It will be appreciated that nonbiodegradable polymers incorporating chemotherapeutic agents are also within the scope of the present invention.

Carrier agents to improve cellular uptake of chemotherapeutic agents can also be incorporated into the periodontal barrier. In one embodiment, the carrier agents can be mixed with the chemotherapeutic agents for delivery by the microparticles in the previously mentioned configurations. In another embodiment, the carrier agents can be separately incorporated into microparticles, which are then combined with the microencapsulated chemotherapeutic agents. In yet another embodiment, the carrier agents can be in the form of a fluid and/or gel positioned with the weave or netting of the periodontal barrier. In still another embodiment, a cross-linked, polymerized form of the carrier agent can be utilized to form the body of the periodontal barrier.

Preferred carrier agents include, without limitation, hyaluronic acid, salts thereof such as sodium hyaluronate, esters, ethers, enzymatic derivatives and cross-linked gels of hyaluronic acid and chemically modified derivatives of hyaluronic acid such as hylan. As used herein, hyaluronic acid broadly refers to naturally occurring, microbial and synthetic derivatives of acidic polysaccharides of various molecular weights constituted by residues of D-glucuronic acid and N-acetyl-D-glucosamine.

Figures 6A, 6B, 6C:
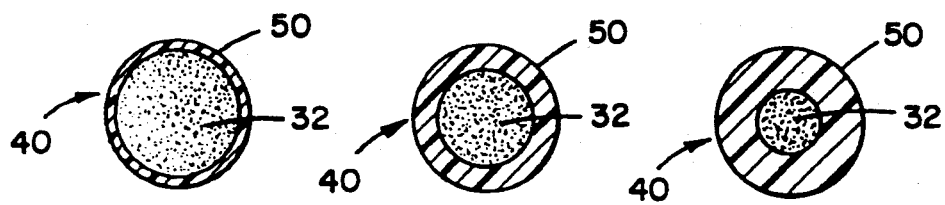
FIGS. 6A through 6C are diagrammatic sectional views of alternate embodiments of microparticles having a somewhat spherical configuration with outside walls of vary thicknesses so as to provide for different timed release of chemotherapeutic agents and optional carrier agents from inside the microparticles.

Referring now to FIGS. 6A-6C, wherein is illustrated diagrammatic sectional views of alternative embodiments of microspheres in accordance with the present invention. The microspheres 40 have a polymer wall or shell 50 which surrounds the chemotherapeutic and optional carrier agents 32, or matrix containing the chemotherapeutic and optional carrier agents. Thus, the walls of the microspheres, as generally illustrated in FIGS. 6A through 6C, may have varying thicknesses and/or be made of a different material to provide for release of the agent continuously or periodically over an extended time period following surgical placement of the periodontal barrier. For example, a barrier may contain an antibiotic which would be released from one type of microparticle during the first critical days following surgery, whereas an anti-inflammatory agent contained in a second type of microparticle would be released for several weeks after implantation. Furthermore, a carrier agent may also be provided with the microencapsulated chemotherapeutic agents to enhance the cellular uptake of the antibiotic and anti-inflammatory agents at the periodontal treatment site. In addition, it is to be understood that the chemotherapeutic agents and optional carrier agents contained within the microspheres may occur in any appropriate medium, such as aqueous, gelatinous, colloidal or semi-solid media.

Incorporation of an antibiotic, such as tetracycline, would help to minimize the infection potential and augment surgical healing. In addition, incorporation of anti-inflammatory agents, such as a nonsteroidal anti-inflammatory drug (e.g. flurbiprofen, meclofenamic acid, etc.) would help to minimize post-surgical swelling and discomfort. Moreover, a sustained, controlled delivery and enhanced cellular uptake to the local site provides significant advantage over systemic dosages of these drugs. In addition, various chemotherapeutic agents and optional carrier agents can be positioned at different strategic areas of a periodontal barrier relative to their intended use. For example, an antibiotic, alone or in combination with an ester of hyaluronic acid, could be positioned with the body of a periodontal barrier 20 for guided tissue regeneration, while an antiplaque agent could be positioned within the beaded rim of the barrier 21 which collars the crown-root junction of the tooth when surgically placed.

It will be further appreciated that the particular chemotherapeutic agents and optional carrier agents utilized as well as the dosages and durations of treatment will be in accordance with accepted treatment. The present invention addresses the manner in which the chemotherapeutic and optional carrier agents are delivered to the local treatment site.

Illustrated in FIGS. 7A through 7D, are various chemotherapeutic agent release patterns which might be achieved using the principles of the present invention.

Figure 7A:
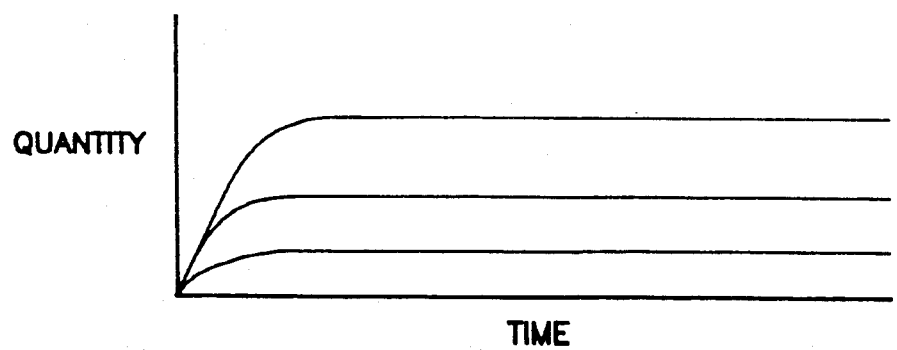
FIGS. 7A through 7D illustrate varying chemotherapeutic agent release patterns.
Figure 7B:
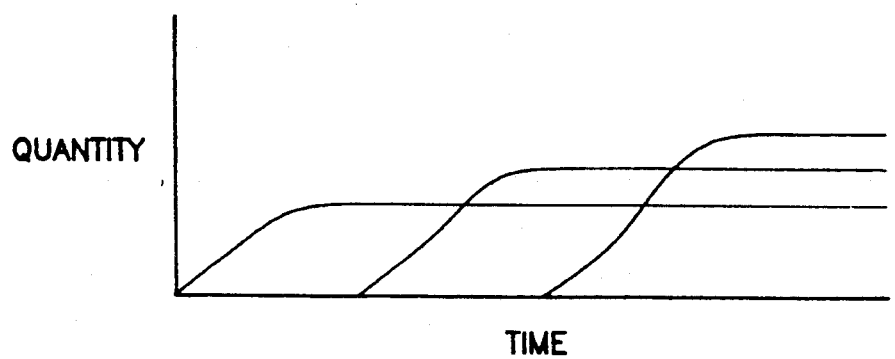
Figure 7C:
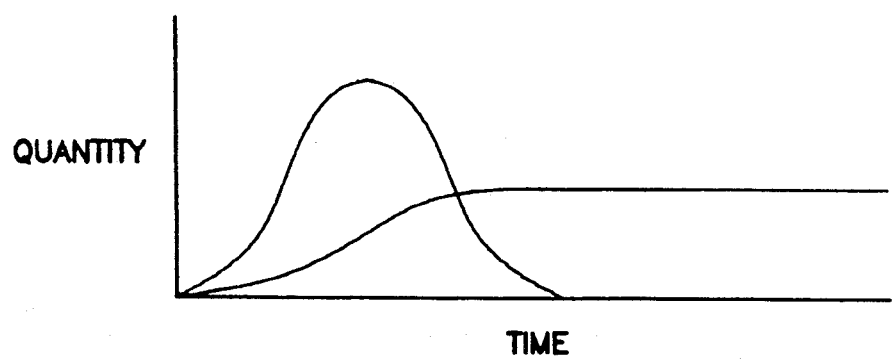
Figure 7D:
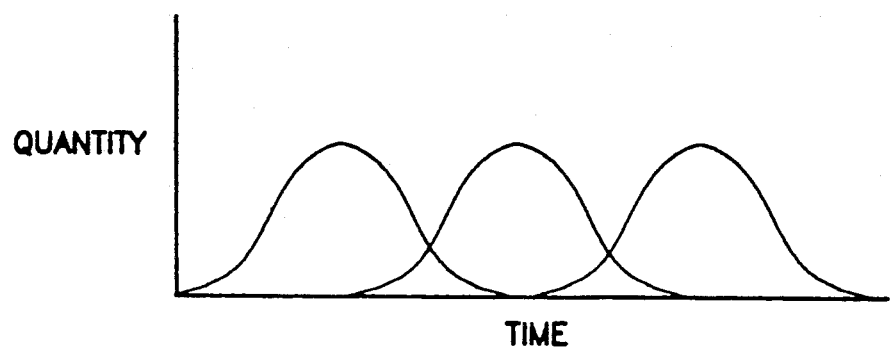

The charts shown illustrate quantity or dosage of the chemotherapeutic agent released over time. In FIG. 7A, three separate chemotherapeutic agents are illustrated as being released at three different substantially constant levels. For example, an antibiotic, anti-inflammatory and tissue regenerative agent may all be released at varying levels at the implantation site. In FIG. 7B, three different chemotherapeutic agents are released at different times. Thus, in accordance with the previous example, the antibiotic may be released first to control post-operative infection, followed by the anti-inflammatory agent to control swelling, and finally by a tissue regenerative agent to aid in healing. In FIG. 7C, a first chemotherapeutic agent is illustrated as being released very early in time and then a second chemotherapeutic agent is released at a substantially constant level for a sustained period of time. An initial high dose release of an antibiotic, followed by a sustained and lower release dose of an anti-inflammatory agent would be illustrative of such a pattern. Finally, FIG. 7D illustrates three different chemotherapeutic agents being released at different times. Such an impulse release pattern may prove particularly useful with a drug which exhibits toxic effects at sustained high dosages or whose efficacy diminishes if administered continuously over a sustained period of time.

It is to be understood, however, that even though numerous characteristics and advantages of the invention have been set forth in the foregoing description, together with details of the structure and function of the invention, the disclosure is illustrative only, and changes may be made in detail, especially in matters of shape, size and arrangement of parts within the principle of the invention, to the full extent indicated by the broad general meaning of the terms in which the appended claims are expressed.

I claim:

1. A method for aiding and guiding periodontal tissue regeneration, comprising the steps of:
  incorporating at least one carrier agent and time-release microshapes encapsulating at least one chemotherapeutic agent into a biocompatible periodontal barrier so as to provide for sustained, controlled delivery and improved cellular uptake of said at least one chemotherapeutic agent to a localized periodontal regeneration site in a mammalian body; and
  implanting said barrier at said localized periodontal regeneration site, wherein said time-release microshapes will begin to release said at least one chemotherapeutic agent at said localized periodontal regeneration site in a sustained, controlled manner, and further wherein said at least one carrier agent will provide for the improved cellular uptake of said at least one chemotherapeutic agent at the localized periodontal treatment site.

2. The method of claim 1 wherein the carrier agent is hyaluronic acid or a derivative thereof.

3. The method of claim 2 wherein the carrier agent is encapsulated in a time release microshape.

4. The method of claim 2 wherein the carrier agent is mixed with at least one chemotherapeutic agent and encapsulated in said time-release microshape prior to incorporating said time-release microshape into said implant.

5. The method of claim 1 wherein the incorporating step includes selecting a biocompatible barrier which is nonresorbable.

6. The method of claim 5 wherein said incorporating step includes selecting a biocompatible, nonresorbable barrier composed of a material selected from the group consisting of polytetrafluoroethylene, dacron, proplast, polypropylene and ethers of hyaluronic acid.

7. The method of claim 1 wherein the incorporating step includes selecting a biocompatible barrier which is resorbable.

8. The method of claim 7 wherein the incorporating step includes selecting a bicompatible, resorbable barrier from the group consisting of crosslinked collagen or esters of hyaluronic acid.

9. The method of claim 1 wherein the incorporating step includes selecting microshapes from the group consisting of microspheres, microfibrils, microfibers, hollow microfibers and microsponges.

10. The method of claim 9 wherein the incorporating step includes selecting microshapes from the group consisting of microspheres sized between approximately 10 to 700 microns in diameter and hollow microfibers having a crosssectional diameter between approximately 100 to 1000 microns.

11. The method of claim 1 wherein the incorporating step includes selecting time-release microshapes encapsulating said chemotherapeutic agents which have time release values, thereby assuring generally continuous release of said chemotherapeutic agents over a predetermined period of time.

12. The method of claim 11 wherein the incorporating step includes mixing said chemotherapeutic agent with a polymer comprising said time-release microshape.

13. The method of claim 12 wherein the mixing step includes selecting a biocompatible, non-resorbable polymer.

14. The method of claim 12 wherein the mixing step includes selecting a biodegradable, resorbable polymer.

15. The method of claims 13 or 14 wherein the mixing step includes selecting the polymer from the group consisting of collagen, cellulosic polymers, ethylene vinyl acetate, methacrylate polymers, lactic glycolic acid polymers, polycaprolactone, polylactides, polystyrene, polycarbonate, polysulfone, polyurethane, esters of hyaluronic acid and ethers of hyaluronic acid.

16. The method of claim 1 wherein the incorporating step includes selecting microshapes for incorporation into said barriers which are surrounded by a polymeric wall or shell, thereby providing for continuous or periodic release of said chemotherapeutic agents over a predetermined period of time.

17. The method of claim 1 wherein the incorporating step includes selecting the chemotherapeutic agent from the group consisting of antibacterial, antibiotic, anti-inflammatory and tissue regenerative agents.

18. The method of claim 17 wherein the incorporating step includes selecting the antibacterial agent from the group consisting of bisbiguanides, fluorides, iodine, heavy metal salts and sulfonamides.

19. The method of claim 17 wherein the incorporating step includes selecting the antibiotic agent from the group consisting of vancomycin, tetracycline, penicillin, cephalosporins, erythromycin, metronidazole, neomycin and kanamycin.

20. The method of claim 17 wherein the incorporating step includes selecting the anti-inflammatory agent from the group consisting of steroidal anti-inflammatory agents and nonsteroidal anti-inflammatory agents.

21. The method of claim 20 wherein the incorporating step includes the a nonsteroidal anti-inflammatory agent from the group consisting of indomethacin, flurbiprofen, meclofenamic acid, ibuprofen and naproxen.

22. The method of claim 17 wherein the incorporating step includes selecting the steroidal anti-inflammatory agent from the group consisting of cortisone, hydrocortisone, beta-methasone, dexamethasone and prednisolone.

23. The method of claim 17 wherein the incorporating step includes selecting the tissue regenerative agent from the group consisting of fibronectin and bone morphogenic protein.

24. The method of claim 1 wherein the barrier comprises a body compatible material with a microstructure, and wherein the incorporating step is selected from the group consisting of incorporating said microshapes into said barrier by extruding said microshapes into the microstructures of said barrier, weaving said microshapes into the microstructure of said barrier, mixing said microshapes with a fluid and/or gel and flowing them into the microstructure of said barrier, placing said microshapes between one or more layers of said barrier and positioning said microshapes between said barrier and an elastomer coating covering said barrier.

25. The method of claim 24 wherein the fluid is hyaluronic acid and the gel is a cross-linked gel of hyaluronic acid.

26. A method for aiding and guiding periodontal tissue regeneration, comprising incorporating at least one carrier agent and time-release microshapes encapsulating at least one chemotherapeutic agent into a biocompatible periodontal barrier, said barrier upon implanatation providing for sustained, controlled delivery and improved cellular uptake of said at least one chemotherapeutic agent to a localized periodontal regeneration site in a mammalian body.

27. The method of claim 26 wherein the carrier agent is hyaluronic acid or a derivative thereof.

28. The method of claim 27 wherein the carrier agent is encapsulated in a time-release microshape.

29. The method of claim 27 wherein the carrier agent is mixed with the at least one chemotherapeutic agent and encapsulated in said time-release microshapes prior to incorporating said time-release microshapes into the bicompatible periodontal barrier.

30. The method of claim 26 further comprising the step of selecting the microshapes from the group consisting of microspheres, microfibrils, microfibers, hollow microfibers and microsponges before the incorporating step.

31. The method of claim 30 further comprising the step of incorporating at least one predetermined chemotherapeutic agent into the selected microshapes before incorporating the microshapes into the barrier.

32. A periodontal barrier comprising:
a body compatible material with a microstructure configured for aiding and guiding periodontal tissue growth adjacent a tooth; and
at least one carrier agent, and time-release microparticles encapsulating at least one chemotherapeutic agent being incorporated into said microstructure, wherein said time release microparticles will begin to release said chematherapeutic agent at a localized periodontal tissue regeneration site upon surgical implanatation of said periodontal barrier, and further wherein said at least one carrier agent will provide for the improved cellular uptake of said at least one chemotherapeutic agent at the localized periodontal regeneration site.

33. The periodontal barrier of claim 32 wherein the carrier agent is hyaluronic acid or a derivative thereof.

34. The periodontal barrier of claim 33 wherein the carrier agent is encapsulated in a time-release microparticle.

35. The periodontal barrier of claim 33 wherein the carrier agent is mixed with the at least one chemotherapeutic agent and encapsulated in said time-release microparticles prior to incorporating said time-release microparticles into the microstructure of the periodontal barrier.

36. The barrier of claim 32 wherein the barrier is constructed of a biodegradable, resorbable material.

37. The barrier of claim 36 wherein said biodegradable, resorbable material is cross-linked collagen or an ester of hyaluronic acid.

38. The barrier of claim 32 wherein the barrier is constructed of a biocompatible, nonresorbable material.

39. The barrier of claim 38 wherein said biocompatible, nonresorbable material is selected from the group consisting of polytetrafluoroethylene, dacron, proplast, polypropylene and an ether of hyaluronic acid.

* * * * *

UNITED STATES PATENT AND TRADEMARK OFFICE
CERTIFICATE OF CORRECTION

PATENT NO. : 5,059,123

DATED : October 22, 1991

INVENTOR(S) : Gary R. Jernberg

It is certified that error appears in the above-identified patent and that said Letters Patent is hereby corrected as shown below:

In Column 3, Line 20, after the word "DESCRIPTION", insert the words --of the INVENTION--.

In Column 3, Line 37, "noneresorbable" should read --nonresorbable--.
In Column 8, Line 21, "crossectional" should read --cross-sectional--.
In Column 9, Line 19, "microstructures" should read --microstructure--.
In Column 9, Line 2, insert --selecting-- after the word "includes".

In Column 2, Lines 24 and 25, "antiinflammatory" should read --anti-inflammatory--.
In Column 3, Line 15, "vary" should read --varying--.
In Column 3, Line 48, "smoothed" should read --smooth--.
In Column 9, Line 2, delete "a" after the word "the".

Signed and Sealed this

Twentieth Day of April, 1993

Attest:

MICHAEL K. KIRK

Attesting Officer

Acting Commissioner of Patents and Trademarks